United States Patent
Takenaga

(10) Patent No.: US 6,868,850 B2
(45) Date of Patent: Mar. 22, 2005

(54) HERNIAL TRUSS

(76) Inventor: Masaharu Takenaga, 67 Starr Ave., Turlock, CA (US) 95380

( * ) Notice: Subject to any disclaimer, the term of this patent is extended or adjusted under 35 U.S.C. 154(b) by 206 days.

(21) Appl. No.: 10/244,370

(22) Filed: Sep. 16, 2002

(65) Prior Publication Data

US 2003/0172923 A1 Sep. 18, 2003

(30) Foreign Application Priority Data

Mar. 18, 2002 (JP) ........................................ 2002-075107

(51) Int. Cl.[7] .................................................. A61F 5/24
(52) U.S. Cl. ..................... 128/96.1; 128/98.1; 128/846; 128/95.1; 602/67
(58) Field of Search ............................. 128/96.1, 98.1, 128/100.1, 105.1, 876, 846, 847, 848, 95.1, 101.1, 108.1; 602/67, 13, 5; 2/400; 450/122

(56) References Cited

U.S. PATENT DOCUMENTS

| | | | | |
|---|---|---|---|---|
| 2,232,381 A | * | 2/1941 | Grant | 128/108.1 |
| 3,308,813 A | * | 3/1967 | Loeffel | 128/96.1 |
| 3,393,675 A | * | 7/1968 | Trznadel et al. | 128/101.1 |
| 3,577,986 A | * | 5/1971 | Regent | 128/96.1 |
| 4,059,103 A | * | 11/1977 | Glaser | 128/96.1 |
| 4,351,325 A | * | 9/1982 | Walker | 128/96.1 |
| 6,422,242 B1 | * | 7/2002 | Slautterback et al. | 128/846 |

* cited by examiner

Primary Examiner—Fadi H. Dahbour
(74) Attorney, Agent, or Firm—Muramatsu & Associates

(57) ABSTRACT

The abstract of the disclosure has been amended as follows:

A hernial truss securely and constantly applies pressure to the herniated abdominal area of the patient while minimizing the pain and skin irritations during use. The hernial truss is formed with a front member applied to the abdominal area of the patent, a rear member applied to the back of the patient, left and right waistbands attached to the front member, left and right crotch bands attached to the rear member, and a pressing pad attached to the inside of the front member. A lower portion of the rear member is divided to left and right by an upward notch. The front and rear members are fitted with the patient body by the waistbands and the crotch bands, and each crotch band connects the rear member and the front member through the bottom of the patient to press the pressing pad against the herniated abdominal area.

7 Claims, 6 Drawing Sheets

HERNIAL TRUSS

FIELD OF THE INVENTION

This invention relates to a hernial truss capable for correctly and securely pressing a herniated abdominal area of a patient's body without causing pain or irritation to the skin.

BACKGROUND OF THE INVENTION

A patient with inguinal hernias use a hernial truss, which puts pressure on the herniated abdominal area, in order to prevent the internal organs from protruding as well as to reduce the symptoms.

The conventional hernial truss is, for example, a support body structured as an upside down triangle, where a pressing pad or pads are established at the center thereof. Waistbands are provided which are stabilized laterally at the top edge of the support body, and a crotch band is connected perpendicularly to the center of the waistbands. By wrapping the waistbands around the patient's waist and attaching the crotch bands at the back and between the legs to the bottom edge of the support body, the pressing pad (or pads) can be positioned and pressed against the inguinal hernias. The lengths of the waistbands and crotch band are adjusted to fit the patient's body so that the pressure applied to the herniated abdominal area by the pressing pad can be appropriately set.

According to the conventional technology mentioned above, the waistbands and crotch band on the hernial truss are made of thin flat strings, which can cause excessive pain as well as harmful skin symptoms such as scratches and irritations. Further, since the pressing pad is only supported on the support body at three locations connected to the waistbands and crotch band, it can easily displaced from the herniated abdominal area when, for example, the patient exercises, making it difficult to maintain the constant pressure against the herniated abdominal area.

SUMMARY OF THE INVENTION

It is, therefore, an object of the present invention to provide a hernial truss which is capable of correctly and securely applying pressure against the herniated abdominal area of the patient's body.

It is another object of the present invention is to provide a hernial truss which is capable of constantly applying pressure against the herniated abdominal area of the patient's body without displacement even when the patient exercises or moves around.

It is a further object of the present invention is to provide a hernial truss which is capable of constantly applying pressure against the herniated abdominal area while minimizing pain or skin symptoms or irritations.

It is a further object of the present invention is to provide a hernial truss with high performance which can be produced with low cost.

In order to achieve the above object, the hernial truss of the present invention is comprised of a front member that is applied to an abdominal area of a patient, a rear member which is symmetrical to the front member and is applied to the back of the patient, left and right waistbands that are attached to lower edges of the front member, left and right crotch bands that are attached downwardly to the rear member, and a pressing pad that is attached to the inner side of the front member. The front and rear members are fitted with the patient body by the waistbands and the crotch bands, and each crotch band connects the bottom of the rear member and the bottom of the front member through the bottom of the patient to press the pressing pad against the herniated abdominal area.

The front member preferably includes an upward notch at the bottom, and the rear member preferably includes an upward notch at the bottom for partially divide the rear member into left and right. Further, each of the front and rear members is provided with a fastener for connecting the waistband.

The front and rear members are joined at the top edge in a ring-like shape through supplementary bands, which attaches to the front and rear members through fasteners. The pulling direction of each waistband on the front member is adjustable by using a rotatable fastener.

According to the structure of the present invention, the front member and the rear member which is symmetrical to the front member, are stably fitted with the abdominal area as well as the back of the patient through the waistbands. By joining each crotch band from the bottom of the rear member to the front member through the legs, the pressing pad can be correctly positioned and pressed against the inguinal hernias. The position of the pressing pad can be adjusted on the inside of the front member such that the pressing pad is positioned right on the treatment spot, i.e., the herniated abdominal area.

The front and rear members can be securely fitted with the patient's body at the appropriate location through the waistbands by having surface fasteners to which each end of those waistbands is attached.

The front and rear members can be quickly and easily set on the patient's waist, abdomen, and back, by joining the top edges in a ring-like manner through the supplementary bands. The front and rear members can be joined by one ring-like supplementary band with moderate elasticity, or by two elastic supplementary bands divided on the left and right sides. The entire length of such divided supplementary bands can be freely adjusted by attaching each end to the front and rear members through the fasteners.

By adjusting the pulling direction from the front member in an up or down direction with use of the rotatable fasteners, each waistband can be wrapped around the patient's waist according to his/her physical shape without any difficulty. The non-adjustable waistbands are preferably fixed to the lower portion of the front member in an upward diagonal direction.

BRIEF DESCRIPTION OF THE DRAWINGS

FIGS. 4A and 4B are front views thereof and FIG. 4C is a rear view thereof.

DETAILED DESCRIPTION OF THE INVENTION

Figure 1:
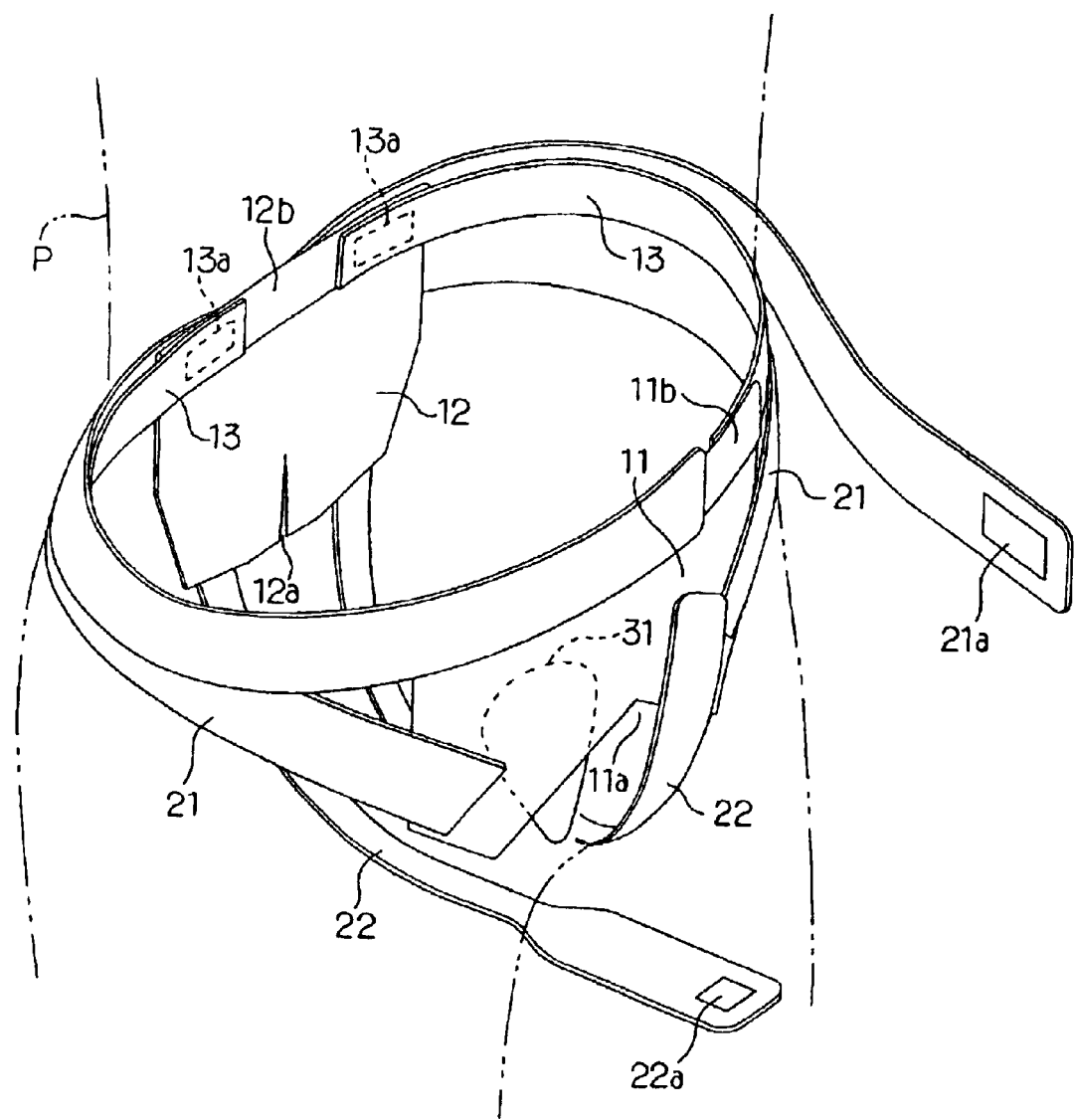
FIG. 1 is a perspective view showing an overall structure and components of the hernial truss of the present invention in a manner used on a patient.

The embodiment of the present invention will be explained in detail below with reference to the accompanying drawings. As shown in the perspective views of FIGS. 1 and 2, the hernial truss of the present invention is comprised of a front member 11, a rear member 12, left and right waistbands 21 attached to the lower portion of the front member 11, left and right crotch bands 22 attached downwardly to the rear member 12, and a pressing pad 31 attached to the inside of the front member 11.

The front member 11, rear member 12, left and right waistbands 21, and left and right crotch bands 22 are made of inextensible fiber sheet material having sufficient pulling strength, which may be reinforced with threads (not shown). One end of each waistband 21 and each crotch band 22 is attached to the front member 11 and the rear member 12, respectively, by sewing for example.

Figure 2:
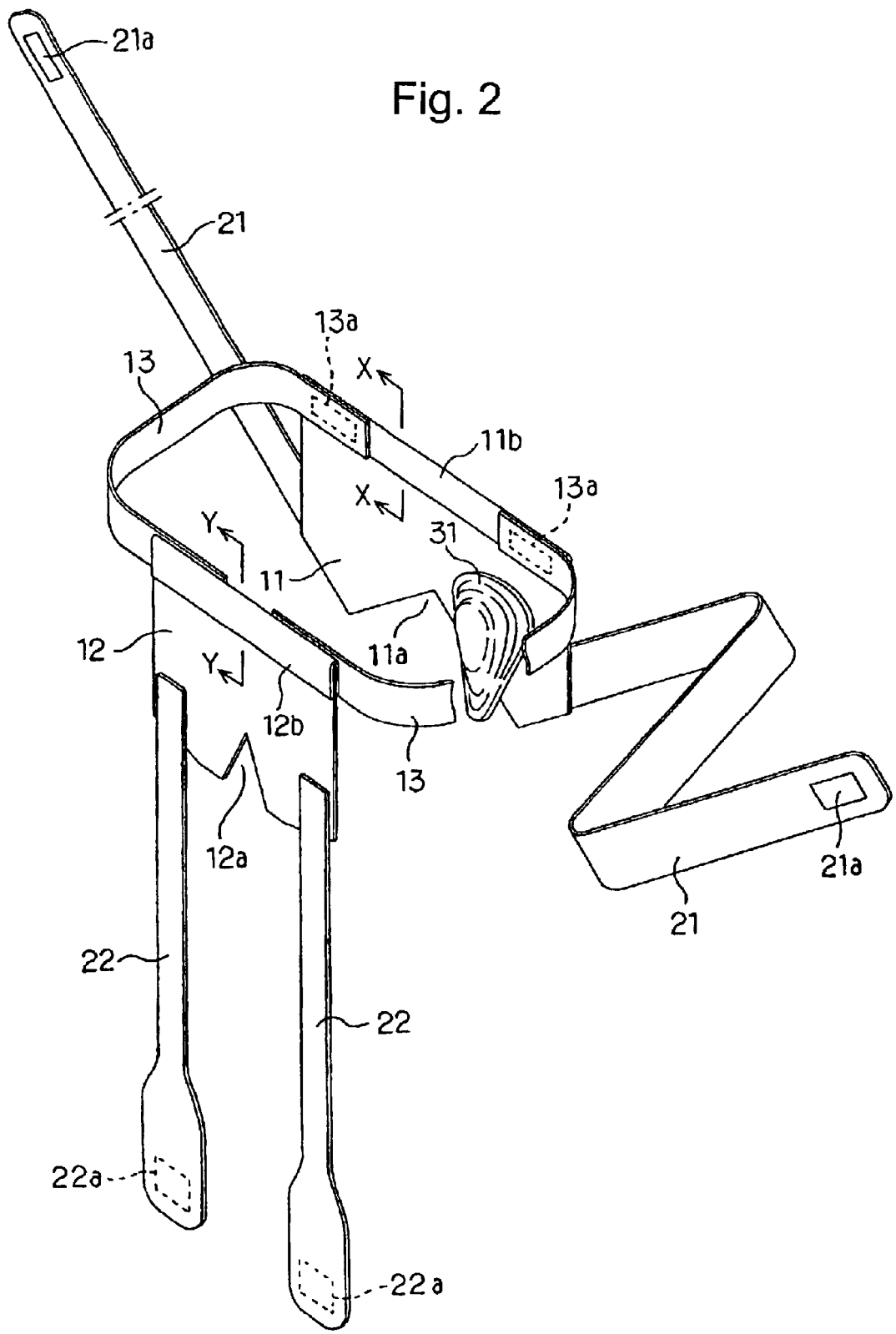
FIG. 2 is a perspective view showing an entire structure and components of the hernial truss of the present invention.
Figure 3A:
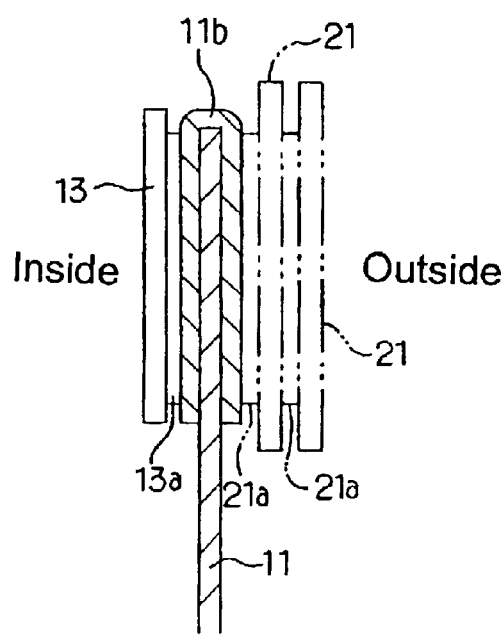
FIG. 3A is a cross sectional view of the hernial truss of the present invention taken along the X—X line of FIG. 2.
Figure 3B:
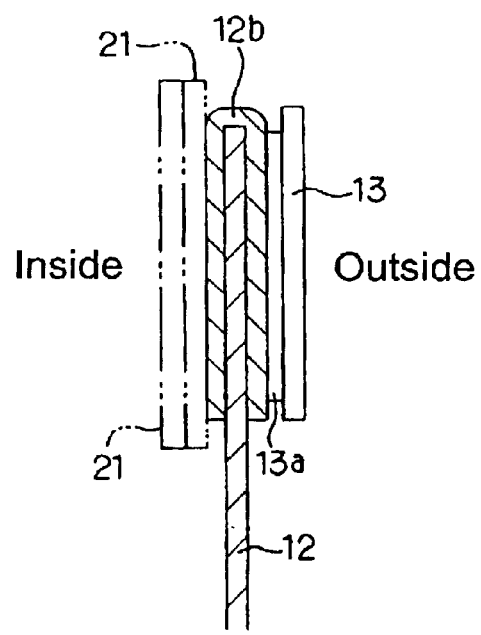
FIG. 3B is a cross sectional view of the hernial truss of the present invention taken along the Y—Y line of FIG. 2.

As seen in FIGS. 1 and 2, a notch or cut-out 11a in the shape of a triangular hill is formed at the bottom of the front member 11, and the left and right side of the notch 11a are cut in an upwardly diagonal direction. FIGS. 3A and 3B are enlarged cross sectional views corresponding to the X—X line and Y—Y line, respectively, of FIG. 2. On the front member 11, a fastener 11b is folded over and attached to the inside and outside of the top straight edge of the front member 11 as best seen in FIG. 3A. The waistbands 21 have a relatively large width and are respectively attached to the left and right sides of the outer bottom edge of the front member 11 in an upwardly diagonal direction, and a fastener 21a is formed on each end of the waistbands 21.

The rear member 12 is formed in a rectangular shape, and is smaller than the front member 11. As seen in FIGS. 1 and 2, a notch 12a is formed in an upside-down narrow letter V at the bottom center of the rear member 12. A fastener 12b is folded over and attached to the inside and outside of the top edge of the rear member 12 as best seen in FIG. 3B. The crotch bands 22 are attached in a downward manner on the left and right sides of the notch 12a at the outer bottom edge of the rear member 12. Each end of the crotch band 22 is enlarged its width and a fastener 22a is formed thereon.

The top of the front member 11 and the top of the rear member 12 are attached to one another in a ring shape through left and right supplementary bands 13 (FIGS. 1 and 2). Each supplementary band 13 has appropriate elasticity, and is attached to the inside of the front member 11 and rear member 12 in a separable manner through a fastener 13a on each end of the supplementary band 13, the fastener 11b on the front member 11, and the fastener 12b on the rear member 12.

The pressing pad 31 is made of moderately firm cushion material, and has a smooth pyramidal or cone shape where the center is higher than the peripheral and is longer in the vertical direction. Further, the pressing pad 31 is attached in a detachable manner to the inside of the front member 11 through a fastener (not shown). The pressing pad 31 can also be arranged in a smooth step-like pattern, with moderately moisture and water absorbent, by stacking up similar flat cushion materials in the order of size and coating them with a fabric surface member.

The front member 11 and waistbands 21 use a surface material, which allows the fasteners 12b, 21a, and 22a to be attached in a detachable manner. The fasteners 13a and 21a are attached with sufficient strength yet in a detachable manner, unlike the fasteners 11b and 12b.

The front member 11 is formed of a fabric sheet that is large enough to cover the abdominal area, and the rear member which is also formed of a fabric sheet to cover the portion right above the rear end and is slightly smaller in width than the front member. By having the waistbands with a relatively large width, for example 4–8 cm, pain from wearing the truss can be minimized.

The front member 11 and the rear members 12 are made of inextensible sheet material having vegetable fiber such as cotton and hemp, animal fiber such as sheep wool and silk, cellulose type regenerated fiber, semi synthetic fiber, non-woven fabric or raising fabric of synthetic fiber such as nylon, acrylic, or polyester. Such material should have sufficient pulling strength, good feel and touch, and moderate flexibility, water and moisture absorbency, and air permeability.

Preferably, the waistbands 21 are made of inextensive sheet material, which has sufficient width so that excessive shock will not be applied to the patient's body while achieving sufficient pulling strength, flexibility, and moisture absorbency. The crotch bands 22 are also made of the same sheet material as the waistbands 21, yet has a narrower width than that of the waistbands. The front member 11, rear member 12, waistbands 21, and crotch bands 22 can be made from a single piece of material or several pieces of same or different material that serve the purpose of each required function.

When the notch 11a is established upwardly at the bottom of the front member 11, the patient can easily urinate through the notch 11a without having to remove the crotch bands 22. The notch 11a can be shaped, for example, like a triangular hill as noted above or a circular dome.

By having the upward notch 12a at the bottom of the rear member 12 which partially separates the lower portion of the rear member 12 to the left and right, when each crotch band 22 connected to the rear member 12 passes between the patient's legs, wrinkles will not be created between those crotch bands 22. The notch 12a is formed by simply cutting the bottom center of the rear member 12 upwardly, or cutting the bottom center of the rear member 12 in a narrow upside-down letter V.

Figure 4A:
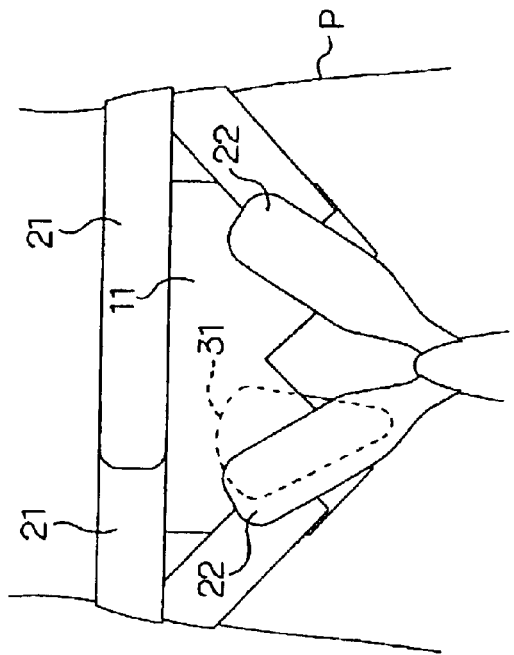
FIGS. 4A–4C show a process for wearing the hernial truss of the present invention on a patient, where

The hernial truss of the present invention constituted as in the foregoing is used in a manner explained below with reference to FIGS. 4A–4C.

First, with the use of the supplementary bands 13, the front member 11 is positioned on the abdominal area of a patient P (FIG. 4A) and the rear member 12 is positioned on the back of the patient P symmetrically to the front member 11. At this point, the supplementary bands 13 are set on the waist of the patient P in order to prevent the front member 11 and the rear member 12 from falling. The pressing pad 31 is adjusted and fixed on the front member 11 so that its position and direction match the inguinal hernias of the patient P.

Figure 4B:
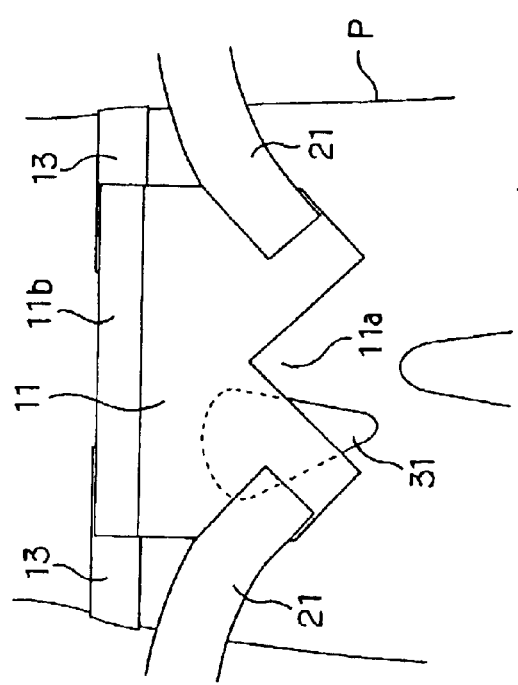
Figure 4C:
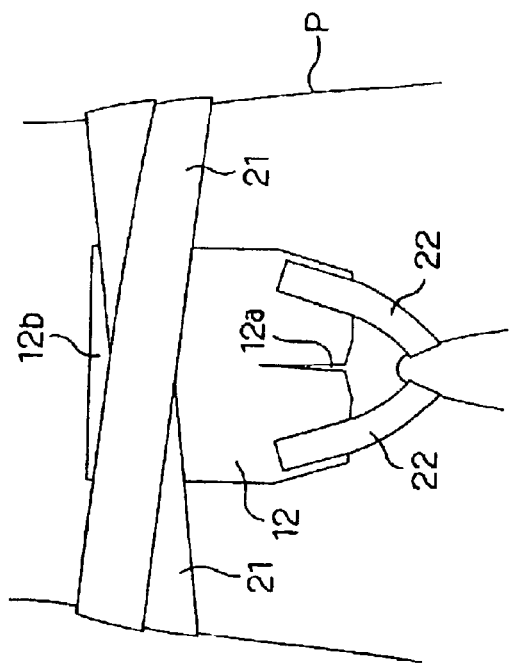

Next, the waistbands 21 are wrapped around the waist of the patient P in the reverse direction from the front to the back and to the front, where each end overlaps one another on the outer top edge of the front member 11 (FIGS. 1 and 4B). At this point, the waistbands 21 are crossed over the fastener 12b of the rear member 12 at the back of the patient P (FIG. 4C and the two-dot chain line in FIG. 3B), and then overlap one another on the fastener 11b of the front member 11 and fastened by the fasteners 21a (FIG. 4B and the two-dot chain line in FIG. 3A).

Therefore, the front member 11 and the rear member 12 are securely fitted on the patient by the waistbands 21 through the fasteners 11b and 12b, and thus, will not shift up and down or left and right. Then, the crotch bands 22 are passed between the legs from the back and attached to the outside bottom of the front member 11 through the fasteners 22a (FIGS. 1 and 4B), which completes the wearing process of the hernial truss. At this point, the end of each crotch band 22 can overlap on the waistbands 21. The hernial truss is preferably worn on underwear (not shown) of the patient P.

When wearing the hernial truss in such a manner, the front member 11 is pulled in four directions by the waistbands 21 and the crotch bands 22, so that whole surface of the front member contacts the abdominal area, thereby allowing the pressing pad 31 to be stably positioned and pressed against the herniated abdominal area. The rear member 12 contacts the back of the patient P symmetrically with the front member 11 via the waistbands 21 and the crotch bands 22.

In other words, the top, left and right sides of the front member 11 is snugly fit with the patient P through the waistbands 21, and the bottom of front member 11 is snugly fit with the patient P through the crotch bands 22. Further, the front member 11 will not be displaced left or right because of the waistbands 21 or up and down because of the crotch bands 22. Accordingly, the pressing pad 31 can be effectively prevented from being displaced from the herniated abdominal area.

When taking the hernial truss off, the fasteners 22a on the crotch bands 22 are unfastened from the front member 11 and the waistbands 21 are unfastened from the front member 11 and the rear member 12.

In the foregoing embodiment of the present invention, the pressing pad 31 can be adhered to either left or right inside of the front member 11, or to both the left and right inside of the front member 11, depending on the location of the inguinal hernias of the patient P.

Figure 5A:
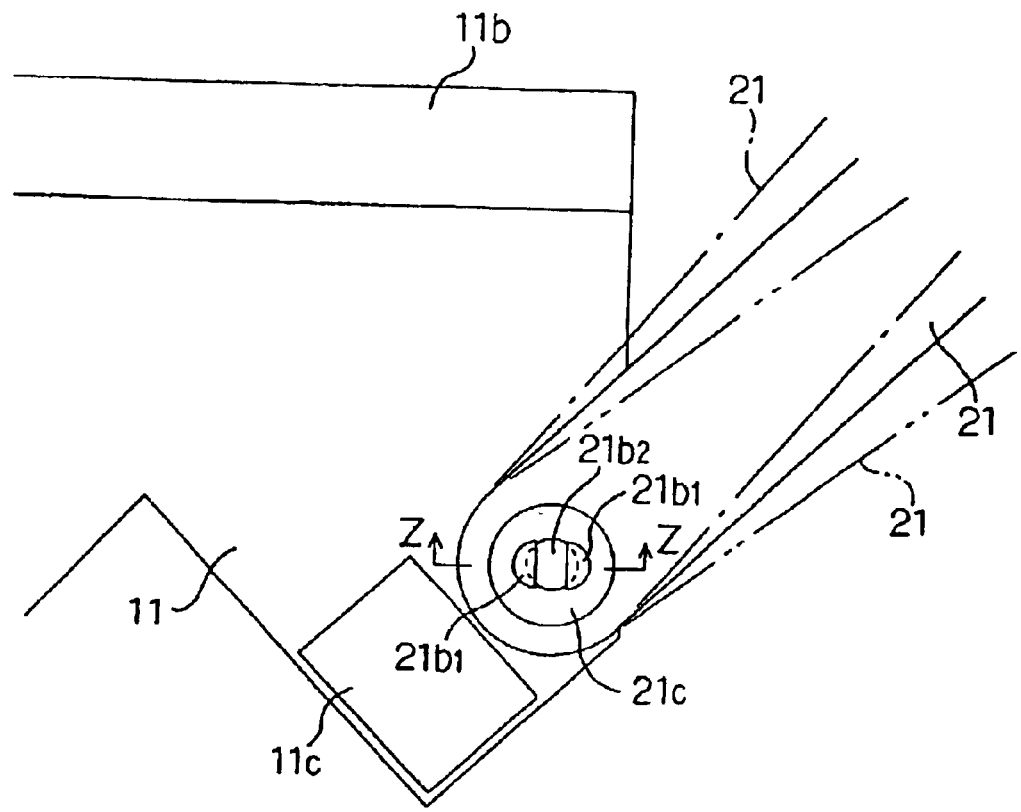
FIGS. 5A and 5B show the essential portions in the modification of the hernial truss of the present invention where FIG. 5A a front view thereof and FIG. 5B is a cross sectional view taken along the Z—Z line of FIG. 5A.
Figure 5B:
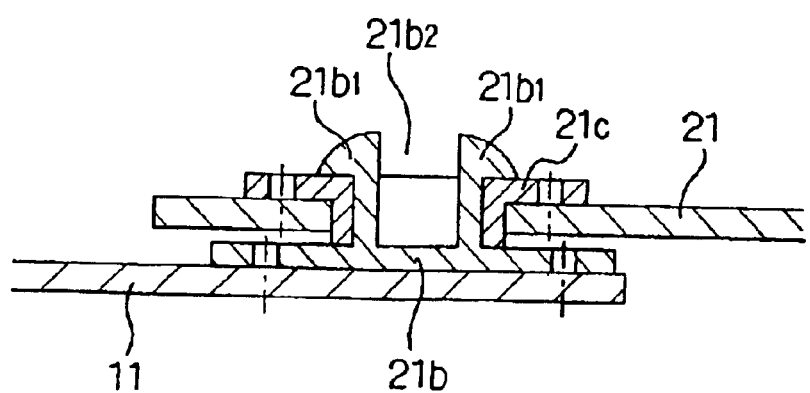

As an alternative aspect, one end of each waistband 21 can be rotatably connected to the front member 11 as shown in FIG. 5A. FIG. 5B is an enlarged cross sectional view of the Z—Z lines of FIG. 5A.

One end of each waistband 21 is joined to the front member 11 by fasteners 21b and 21c, which are snap fit with one another in a rotatable manner. These fasteners 21b and 21c are individually sewn on the front member 11 and the waistbands 21 respectively. A pair of engaging units 21b1 are formed through a slot 21b2 of the fastener 21b. The engaging units 21b1 are elastically fitted in the ring-shaped fastener 21c from the inner side by a single action. In this arrangement, the pulling direction of the waistbands 21 from the front member 11 can be adjusted in up and down directions by the relative pivotal or rotational motion of the fasteners 21b and 21c as expressed by the continuous lines, dashed lines, and two-dot chain lines, respectively, in FIG. 5A.

At the bottom of the front member 11, a reinforcement member 11c can be provided adjacent to the fastener 21b. The reinforcement member 11c prevents the bottom of the front member 11 from rising or deforming.

Figure 6:
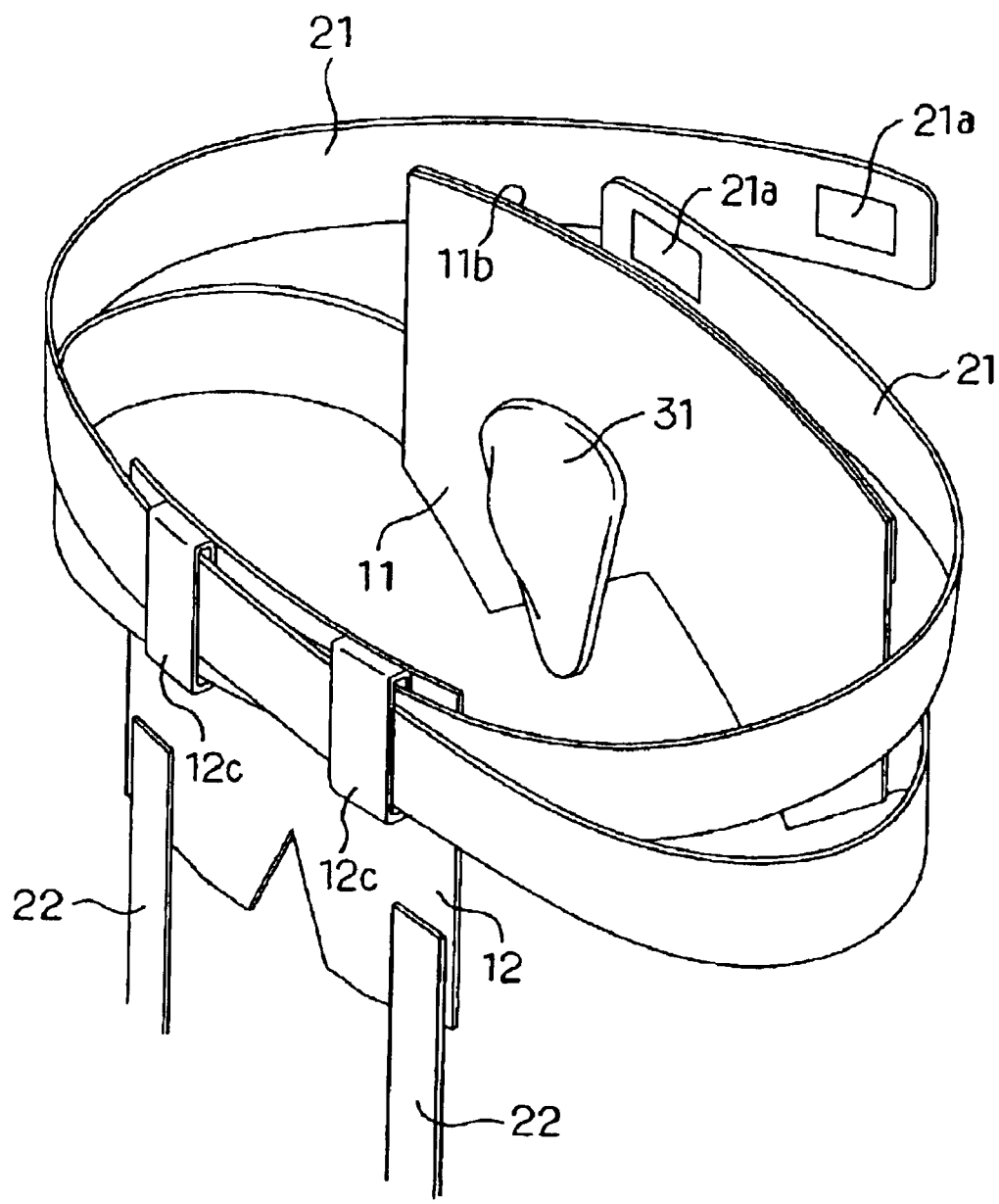
FIG. 6 is a perspective view showing an entire structure of the hernial truss in a further embodiment of the present invention.

In a further aspect, as shown in FIG. 6, the front member 11 and the rear member 12 can be joined in a ring-like shape through the waistbands 21. On the upper outer side of the rear member 12, belt loops 12c, where each waistband 21 is inserted through in the opposite direction from one another, are attached. In this embodiment, the fastener 12b in FIGS. 1–4 is not used at the top edge of the rear member 12, and the fastener 11b is formed only on the outside of the front member 11. Thus, the front member 11 and the rear member 12 can be easily worn on the lower abdominal area and the back of the patient P by overlapping the ends of the waistbands 21 at the top edge of the front member 11 and fastening them.

The pressing pad 31 can be formed to have an entirely smooth outer surface by using a smooth cushion material such as shown in FIG. 6.

In the foregoing embodiments, the hernial truss is preferably constructed without using any metallic material. If such metallic material is used, when a patient P wearing the hernial truss passes through a metal detector in an airport, for example, the detector may be activated, thereby causing unnecessary trouble.

According to the present invention, since the hernial truss is comprised of the front member attached with the left and right waistbands, the rear member attached with the left and right crotch bands, and the pressing pad attached to the front member, the front member and the rear member are securely fixed on the patient's lower abdominal area and the back, respectively. Consequently, the hernial truss will not cause any localized excessive pressure against the patient, and thus, will be painless and harmless to the skin. Further, the pressing pad can correctly and stably press the herniated abdominal area without being displaced or shifted from the herniated part.

Although only a preferred embodiment is specifically illustrated and described herein, it will be appreciated that many modifications and variations of the present invention are possible in light of the above teachings and within the purview of the appended claims without departing the spirit and intended scope of the invention.

What is claimed is:

1. A hernial truss for use by a patent for pressing patient's herniated abdominal area, comprising:
   a front member which is applied to the patient's abdominal area;
   a rear member which is symmetrical to said front member and is applied to the patient's back;
   left and right waistbands which are attached to lower sides of said front member;
   left and right crotch bands which are attached downwardly to said rear member; and
   a pressing pad which is provided on an inside of said front member;
   wherein the front member and the rear member securely fit with the patient's body through said waistbands, and said pressing pad on the front member presses the herniated abdominal area when each of the crotch bands connects the bottom of the rear member and the bottom of the front member through the bottom of the patient; and
   wherein a lower portion of said rear member is divided to left and right by an upward notch.

2. A hernial truss as defined in claim 1, wherein said front member has an upward notch at the bottom thereof.

3. A hernial truss as defined in claim 1, wherein a fastener is provided on each surface of the front member and the rear member to fasten with each end of said waistbands.

4. A hernial truss as defined in claim 1, wherein said front member and said rear member are joined in a ring-like shape through supplementary bands.

5. A hernial truss as defined in claim 4, wherein said supplementary bands are attached to the front member and the rear member through fasteners.

6. A hernial truss as defined in claim 1, wherein each of said waistbands is fixedly connected to the front member in an upward diagonal direction.

7. A hernial truss as defined in claim 1, wherein each of said waistbands is connected to the front member through a rotatable fastener so that its pulling direction is adjustable.

* * * * *